United States Patent
Taskin

(10) Patent No.: US 10,029,040 B2
(45) Date of Patent: Jul. 24, 2018

(54) IMPLANTABLE PUMP WITH TAPERED DIFFUSER REGION

(71) Applicant: HeartWare, Inc., Miami Lakes, FL (US)

(72) Inventor: Mustafa Ertan Taskin, Cooper City, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 14/822,360

(22) Filed: Aug. 10, 2015

(65) Prior Publication Data

US 2016/0038663 A1 Feb. 11, 2016

Related U.S. Application Data

(60) Provisional application No. 62/035,003, filed on Aug. 8, 2014.

(51) Int. Cl.
   *A61M 1/10* (2006.01)
   *A61M 1/12* (2006.01)

(52) U.S. Cl.
   CPC .............. *A61M 1/122* (2014.02); *A61M 1/10* (2013.01); *A61M 1/1001* (2014.02); *A61M 1/1012* (2014.02); *A61M 1/101* (2013.01); *A61M 1/1008* (2014.02); *A61M 1/1082* (2014.02); *A61M 1/1084* (2014.02); *A61M 1/125* (2014.02)

(58) Field of Classification Search
   CPC ...... A61M 1/10; A61M 1/1001; A61M 1/101; A61M 1/1012; A61M 1/122
   USPC ................................................ 623/3.1–3.28
   See application file for complete search history.

(56) References Cited

U.S. PATENT DOCUMENTS

| | | | |
|---|---|---|---|
| 5,947,892 A * | 9/1999 | Benkowski | A61M 1/10 415/900 |
| 6,135,729 A * | 10/2000 | Aber | A61M 1/10 417/356 |
| 7,699,508 B2 | 4/2010 | Schroeder | |
| 7,972,122 B2 | 7/2011 | LaRose et al. | |
| 8,007,254 B2 | 8/2011 | LaRose et al. | |
| 8,419,609 B2 | 4/2013 | Shambaugh, Jr. et al. | |
| 8,852,072 B2 | 10/2014 | LaRose et al. | |
| 2009/0203957 A1* | 8/2009 | LaRose | A61M 1/101 600/18 |
| 2015/0051438 A1 | 2/2015 | Taskin | |

OTHER PUBLICATIONS

Taskin et al., "Computational Fluid Dynamics Optimization of the Longhorn Transapical Ventricular Assist Device", presentation at meeting of ISRBP, Sep. 2013, 8 pages.

* cited by examiner

*Primary Examiner* — Dinah Baria
(74) *Attorney, Agent, or Firm* — Christopher & Weisberg, P.A.

(57) ABSTRACT

A blood pump, such as an axial flow pump, having a pump housing, the pump housing defining a flow path and having a tapered portion adjacent to an outlet, tapering toward the outlet, an outflow cannula connected to the outlet of the pump housing, and an impeller and diffuser, disposed in the pump housing, the diffuser having a tapered body corresponding to the tapered portion of the pump housing, the diffuser body having at least one vane extending therefrom, the vein tapering in the same direction as the diffuser body. The present invention also includes a method of manufacturing the blood pump and a method of implanting the blood pump.

19 Claims, 12 Drawing Sheets

IMPLANTABLE PUMP WITH TAPERED DIFFUSER REGION

CROSS-REFERENCE TO RELATED APPLICATIONS

The present application claims the benefit of the filing date of U.S. Provisional Patent Application No. 62/035,003 filed Aug. 8, 2014, the disclosure of which is hereby incorporated by reference.

BACKGROUND OF THE INVENTION

In certain disease states, the heart lacks sufficient pumping capacity to meet the needs of the body. This inadequacy can be alleviated by providing a mechanical pumping device referred to as a blood pump, one example of which is a ventricular assist device ("VAD"). A VAD, for example, acts in parallel with a patient's left ventricle to impel blood from the ventricle into the aorta, and thus supplements the pumping action of the heart.

A blood pump is typically connected, e.g., installed, outside of the heart. In the instance of a VAD, it may include an inlet cannula connecting the interior of the left ventricle to the intake of the pump. The VAD may also include an outlet tube connected between the outlet of the pump and the aorta. Once connected to a ventricle, the VAD and the heart act in parallel to pump blood from the left ventricle to the aorta. A blood pump in a typical human patient should be capable of providing substantial blood flow, as, for example, a few liters per minute or more, against a pressure head corresponding to the blood pressure of the patient. For example, one typical operating condition for a blood pump involves pumping 5 liters of blood flow at a pressure head of 75 mmHg. Pressure head is known as the difference in pressure between the outlet and the inlet of the pump, where a positive number indicates higher pressure at the outlet.

Implantable blood pumps should also be compact so as to facilitate mounting the pump within the patient's body. An implantable blood pump should further be efficient so as to minimize the power required to operate the pump, for example, by reducing the rotational speed needed to achieve a particular pressure head. Moreover, the pump should be designed to minimize damage to the patient's blood. It should limit the amount of blood subjected to relatively high shear stresses, for example, 150 Pa or more, so as to minimize the damage to components of the blood. Ideally, and in addition to these attributes, a blood pump should remain in operation for months or years to keep a patient alive, or indefinitely at least until the heart heals or a suitable donor heart becomes available if the heart does not heal.

One form of a blood pump is disclosed in U.S. Pat. No. 8,852,072. The pump includes a pump housing having an impeller and a diffuser disposed within the pump housing. The impeller has a linear body extending along an axis and blades projecting outwardly from the body and curving around the axis in a substantially helical pattern having a pitch angle which varies along the axial length of the impeller. A power source provides the means to actuate the impeller, causing it to impel blood axially in the housing in a downstream direction towards a linear diffuser. The diffuser includes vanes projecting radially outward from the body. The pump generates pressure head for blood entering through an inlet of the housing and exiting into the aortic valve. Although prior art pumps can generate pressure to pump blood, further improvements as described above would be desirable.

Accordingly, there is a need for an implantable blood pump which is sized so that a diffuser region of a housing having a diffuser disposed therein does not extend into an aortic valve when implanted in a ventricle. There is also a need for a pump which produces greater pressure head through the pump relative to prior art designs while simultaneously reducing shear stresses within the housing.

BRIEF SUMMARY OF THE INVENTION

The present invention relates to blood pumps containing a diffuser and methods of manufacturing and using the blood pumps.

One aspect of the present invention provides an implantable blood pump. The pump includes a housing having an intake end and an outflow end, a cannulated tip extending from the outflow end of the housing, an impeller disposed in the housing, and a diffuser disposed in the housing. The diffuser includes a tapered body.

In one embodiment according to this aspect of the invention, the housing can have a first portion adjacent the intake end, a second portion adjacent the outflow end, and a third portion between the first and second portions. A cross-sectional area of the first portion can be greater than a cross-sectional area of the second portion. A cross-sectional area of the third portion can decrease in a direction from the first portion to the second portion. The housing can also be linear.

The diffuser can be disposed in the third portion of the housing. The first, second and third portions can be sized such that when the implantable blood pump is positioned within a left ventricle, only the second portion and the cannulated tip interact with an aortic valve. The cross sectional area of the first, second and third portions can be circular.

An inner surface of the third portion of the housing can taper toward the outflow end in parallel with a surface of the tapered body of the diffuser. This parallel taper can be such that the cross-sectional area of a flow path between the inner surface of the third portion and the diffuser is approximately the same at any point along a length of the tapered body of the diffuser.

In another embodiment, the tapered body of the diffuser can be a truncated cone shape. A cross-sectional area of the tapered body can be largest at an intake end of the tapered body.

A length of the diffuser can be between about 0.50 inches and less than 0.85 inches. The length of the diffuser can also be preferably about 0.55 inches. The diffuser can include a first conically shaped tip extending from the diffuser body towards the outflow end and a second conically shaped tip extending from the diffuser body towards an intake end. The volume of the tips is such that the first conically shaped tip has a volume smaller than a volume of the second conically shaped tip. A length of the first conically shaped tip can be about the same as a length of the second conically shaped tip, wherein such length is measured along a longitudinal axis of the tapered body.

The tapered body of the diffuser in this embodiment can further include at least one vane positioned along a surface defined along a length of the tapered body. The at least one vane can include a peak having a height extending outward in a perpendicular direction from the surface of the tapered body. The height can taper along the length of the tapered body in a direction toward the outflow end. The tapering of the at least one vane along the length of the tapered body can be relative to the surface of the tapered body or relative to a longitudinal axis of the diffuser. A thickness of the at least one vane can be about 0.03 inches.

Another aspect of the present invention provides a method of manufacturing an implantable blood pump. The method includes providing a cannulated tip, a housing having an intake end and an outflow end, an impeller disposed in the housing and a diffuser disposed in the housing. The diffuser includes a tapered body and has a length between about 0.50 inches and less than 0.85 inches. The method further includes attaching the cannulated tip to an outflow end of the housing.

In yet another aspect of the present invention, a method of pumping blood and minimizing exposure to shear stresses is provided. The method includes providing a housing having an intake end and an outflow end, a cannulated tip extending from the outflow end of the housing, an impeller disposed in the housing, and a diffuser disposed in the housing. The diffuser includes a tapered body and has a length between about 0.50 inches and less than 0.85 inches. Then, surgically inserting the pump into an anatomical location in the human body. After inserting the pump, driving the pump using a power source so that blood is drawn into the intake end of the housing and pumped to the outflow end of the housing and through the cannulated tip of the blood pump into the patient's aorta.

DETAILED DESCRIPTION

The term blood pump, pump or device, as used throughout, is intended to refer generally to pumps which may be used within the vasculature, such as within the heart, the aorta, the various arteries or veins, or the like, or adjacent to the vasculature, such as adjacent to the wall of the heart, or within the abdomen adjacent to the heart or other vasculature. Typically, such blood pumps are implanted into the left or right ventricle of the heart and can pump through the aortic valve or a bypass conduit. One exemplary type of blood pump is a ventricular assist device, commonly referred to as a VAD, that is positioned to supplement the pumping of blood from the left ventricle into the aorta. While the blood pump is discussed below relative to its use as a VAD, the blood pump of the present invention may be used and implanted in a variety of anatomical locations to supplement blood flow throughout the vasculature.

Figure 1:
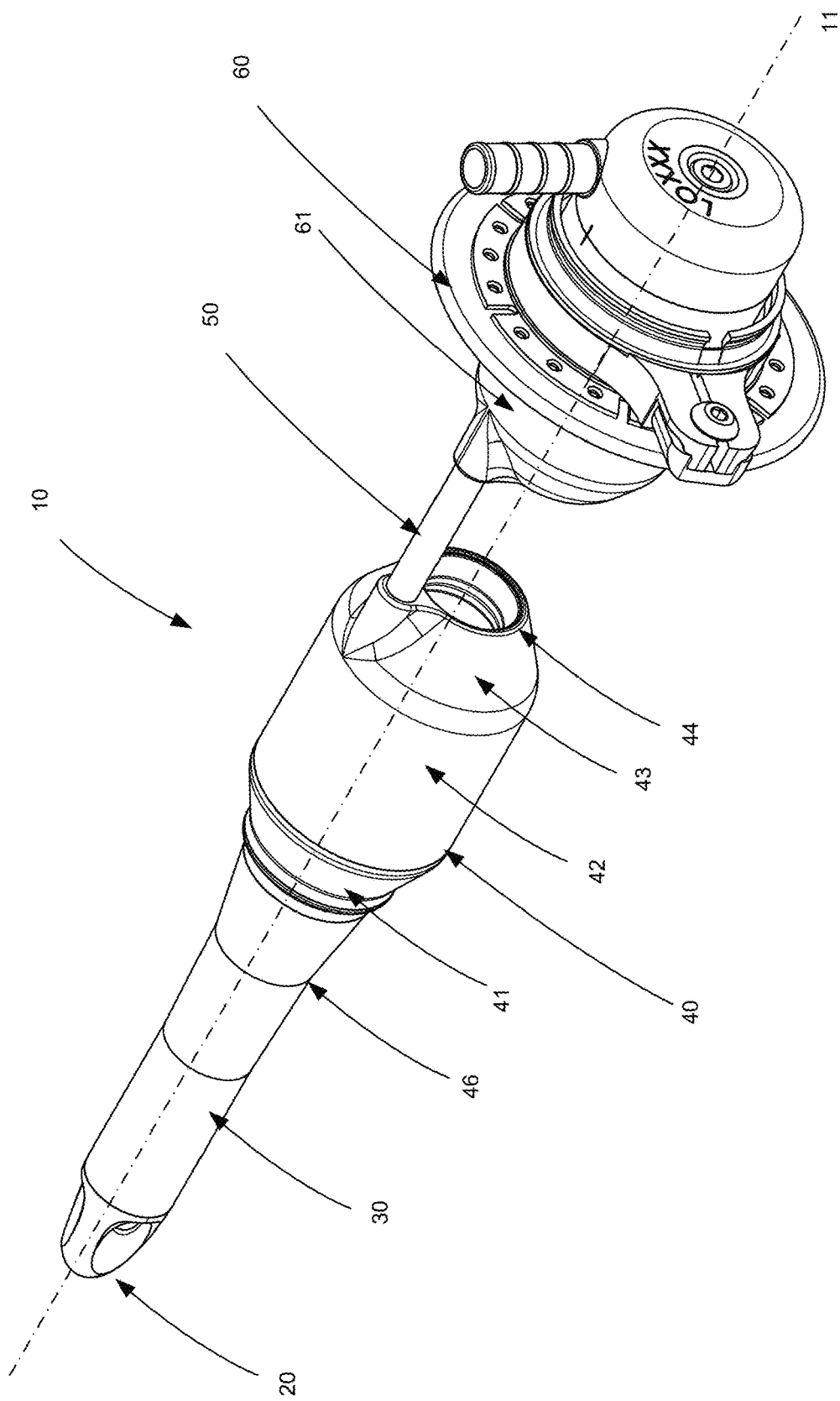
FIG. 1 is an isometric view of the blood pump in accordance with one embodiment of the invention.

Referring to the drawings, wherein like reference numerals refer to like elements, there is shown in FIG. 1 an embodiment of the implantable blood pump of the present invention designated generally by reference numeral 10. Blood pump 10 has four distinct sections including a cannula tip 20, a linear housing, an elongate member 50 and a ring 60. Also in FIG. 1, the linear housing of pump 10 has three distinct portions. These portions include a first portion, also referred to as inlet portion 43 and central portion 42 collectively, a second portion, also referred to as outflow cannula 30, and a third portion, also referred to as outlet portion 41.

Outflow cannula 30 is shown in FIGS. 1-4. Outflow cannula 30 is substantially cylindrical in shape and has a length extending from outlet 46 of pump housing 40 to cannula tip 20. Outflow cannula 30 is substantially in the form of a hollow tube having a first end attached to pump housing 40 communicating with outlet 46 and a second end attached to tip 20. Outflow cannula 30 may be made of materials known to one of ordinary skill in the art, such as those disclosed in U.S. Pat. No. 8,852,072.

Outflow cannula 30 is straight and has an appropriate stiffness and hardness to accommodate the native heart and aortic root geometry and also to have non-traumatic contact with tissues. The outflow cannula 30 is sized so that its cross-sectional shape helps to minimize retrograde flow through the valve due to poor sealing of the tri-leaflets around the cannula, that is to say, minimize aortic valve insufficiency. The illustrated circular cross-sectional shape also minimizes aortic valve insufficiency. The diameter of the outflow cannula relative to the housing is as shown in FIGS. 1, 3 and 4.

As seen in FIG. 1, tip 20 has a circumferential surface which tapers inwardly toward the axis of the cannula in a distal direction, and thus converges toward a distal extremity of the cannula. In the embodiment illustrated in FIGS. 1-4, the distal surface of the tip defines a smooth, dome-like shape at the distal extremity of the tip. The shape of tip 20 can be any known to those of skill in the art. For example, see U.S. Pat. No. 8,852,072.

FIGS. 1, 2, 3 and 4 illustrate one embodiment of the pump housing 40. Pump housing 40 is an axial flow pump housing and defines a flow path 45 therethrough. The pump housing includes an outlet portion 41, a central portion 42, and an inlet portion 43. Outlet portion 41 tapers inwardly from central portion 42 to outlet 46. Inlet portion 43 tapers inwardly from central portion 42 to inlet 44. Each of outlet portion 41, central portion 42 and inlet portion 43 are of circular cross section. The pump housing has a length arranged along an axis 11. As shown in FIG. 1, the axis is linear. The tapered structure of the outlet portion 41 may allow for assembly of a pump housing 40 shorter in length than a pump housing with no tapered outlet portion. For example, when the pump 10 is in the insertion position, only the outflow cannula 30 and cannulated tip 20 might interact with the aortic valve. Additionally, a tapered outlet portion 41 may allow for a diffuser shorter than prior art diffusers to be disposed in the housing. The pump housing 40 is formed from materials known to those of ordinary skill in the art such as those described in U.S. Pat. Nos. 7,972,122, 8,007,254 and 8,852,072.

Figure 3:
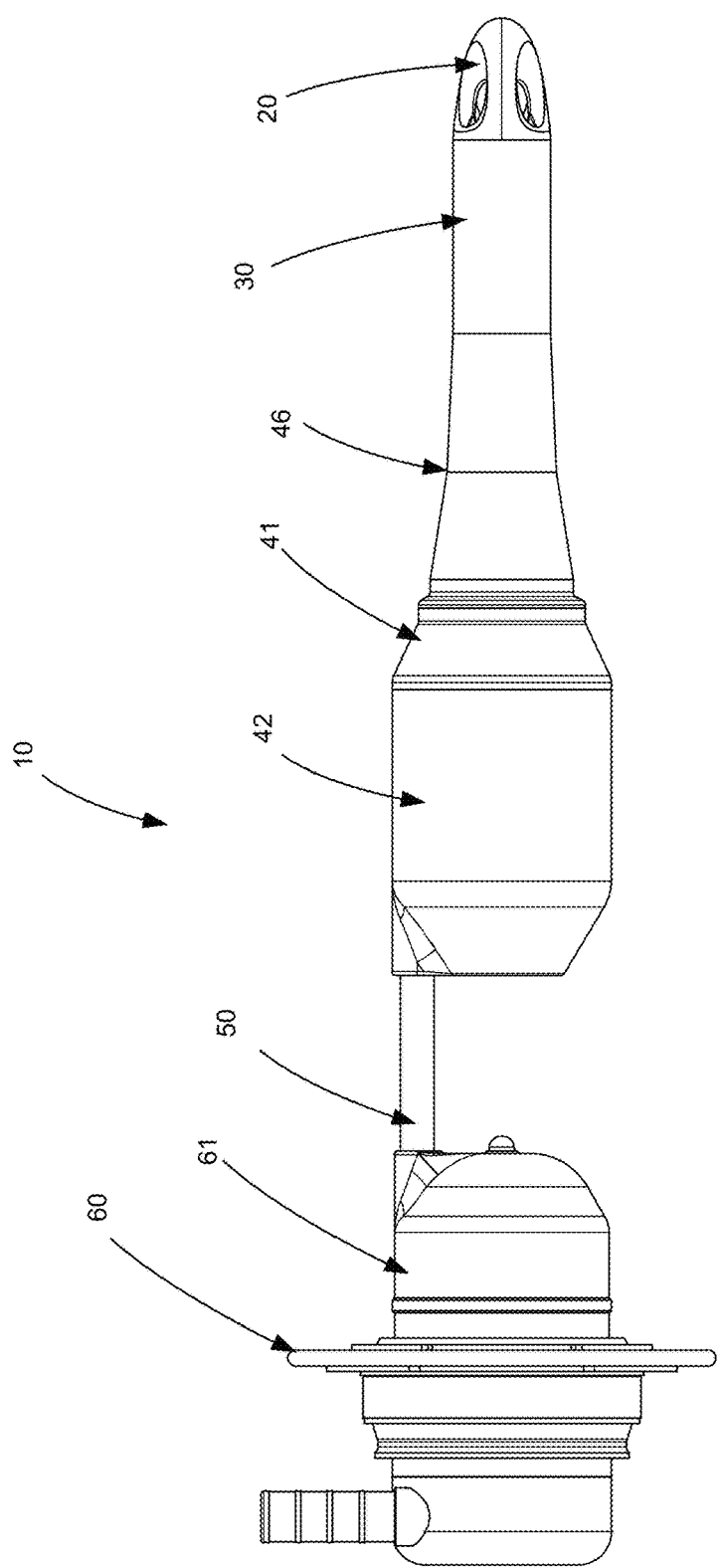
FIGS. 3 and 4 are elevation views of the blood pump depicted in FIG. 1.
Figure 4:
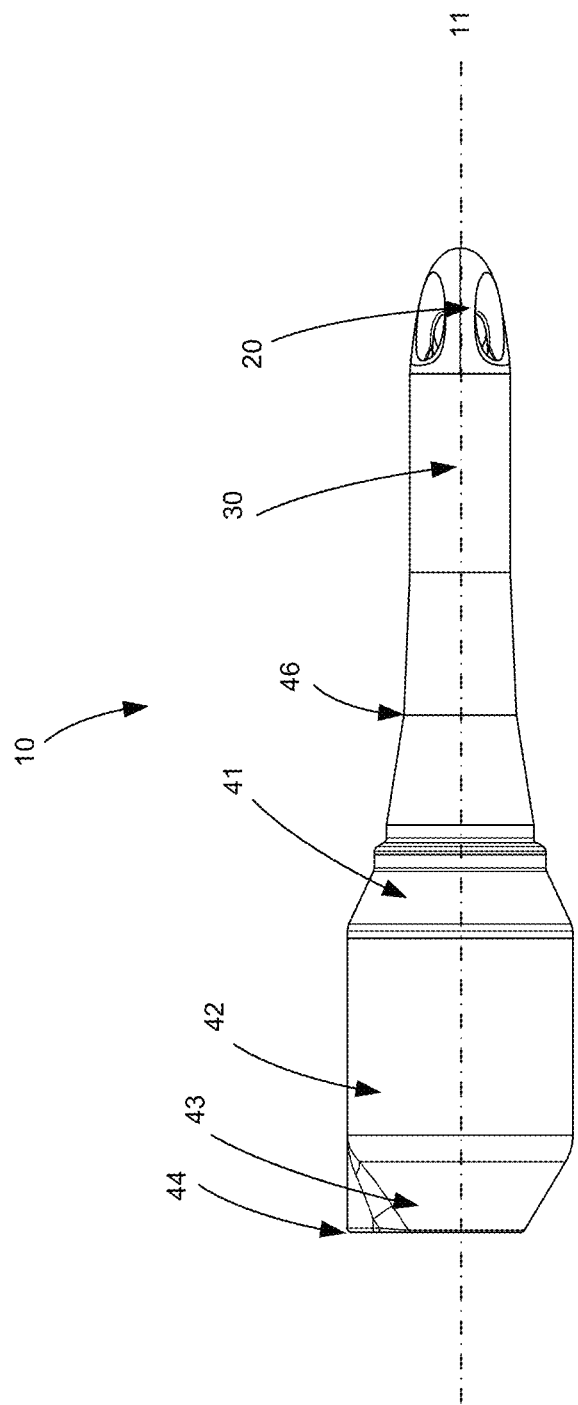

Extension body 50 is shown in FIGS. 1 and 3. Extension body has an axis along its direction of elongation which axis is parallel to the axis 11 of the pump housing 40 but offset from axis 11 in a direction transverse to both axes. Extension body has a length extending from pump housing 40 to a spherical ball 61. Extension body 50 is adjustable both axially and angularly. Extension body is comprised of materials such as those described in U.S. Pat. No. 8,852,072. The extension body 50 is sufficiently rigid to maintain the pump housing 40 in position, with no substantial movement, relative to ring 60 under loads normally applied to the blood pump 10 while the pump is in place within the heart. For example, the extension body 50 can be substantially rigid.

The blood pump 10 also includes an anchoring element in the form of a ring 60. Ring 60 is adapted for mounting adjacent the apex of the patient's heart and includes a spherical socket adapted to engage the spherical ball 61 such that ring 60 is pivotally mounted to extension body 50 remote from pump housing 40. The anchoring element can be any known to those of ordinary skill, such as those described in U.S. Pat. No. 8,852,072.

The blood pump 10 is started by applying power from a power source. For example, pump 10 can be powered through electrical power provided by an external or implantable power source. Power for pump 10 can be provided in ways known to those of ordinary skill in the art. For example, see U.S. Pat. No. 8,852,072.

Figure 2:
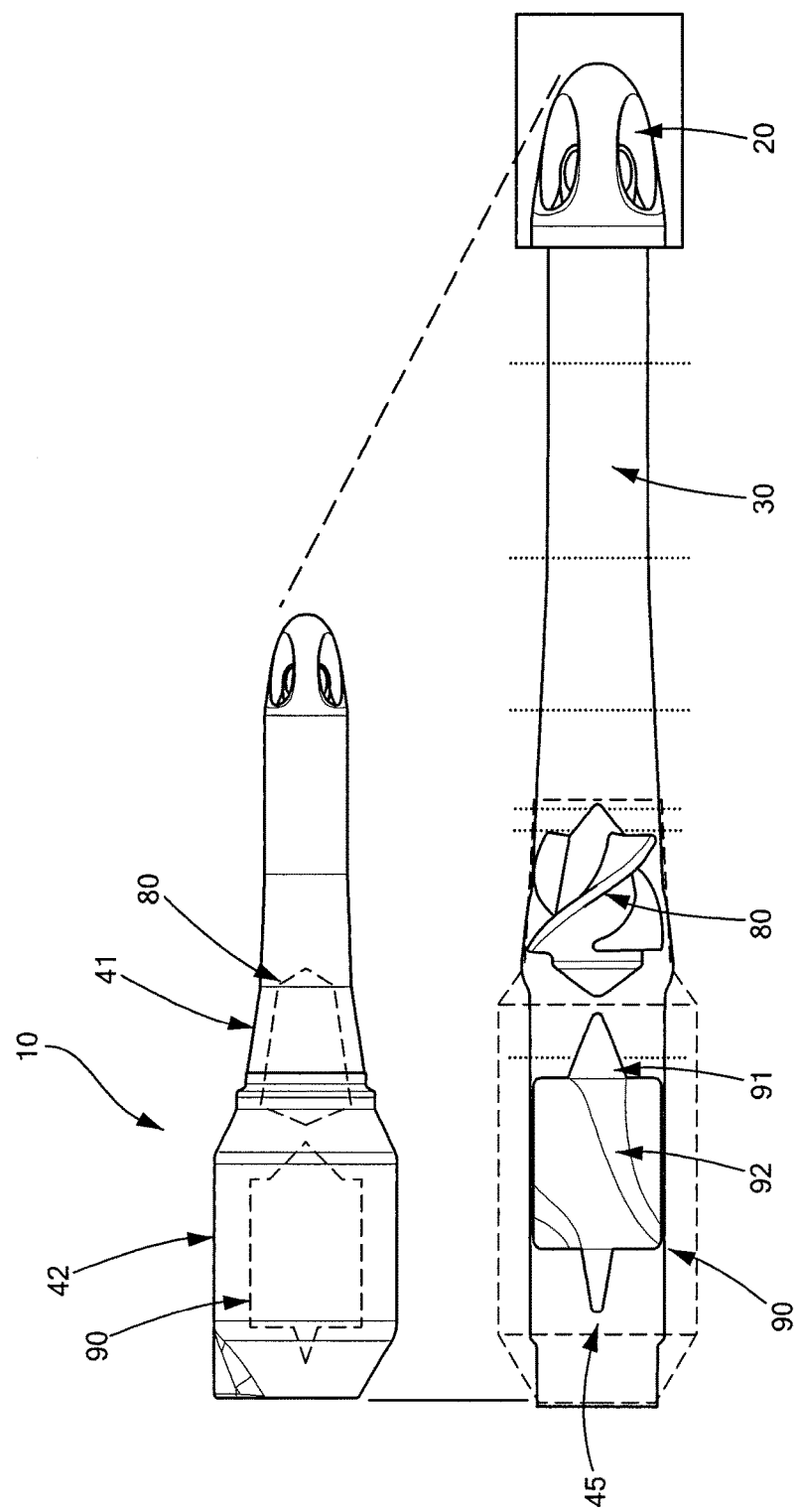
FIG. 2 is a sectional view of a blood pump with an impeller and diffuser depicted in accordance with one embodiment of the invention.

An impeller 90 is disposed within pump housing 40 shown in FIG. 2. The impeller may be at least partially, and preferably entirely, disposed within central portion 42. Impeller 90 includes a body 91 in alignment with pump housing 40 and axis 11. Body 91 includes a plurality of blades 92 projecting outward from the body 91 and curving around the axis in a substantially helical pattern having a pitch angle which varies along the axial length of the impeller 90. The blades 92 define flow channels between them. Impeller 90 is arranged to rotate around axis 11 and to impel blood in axial direction 11 or otherwise in accordance with a longitudinal axis of impeller 90. During operation, the impeller is driven in rotation at a high rotational speed, typically about 8,000 rpm to about 40,000 rpm. The impeller blades 92 impel blood within the pump housing 40 axially, toward the outflow cannula 30. The blood pump 10 is arranged to deliver about 5 L/min flow rate against a pressure head of about 75 mmHg.

Examples of impeller 90 are shown in U.S. Pat. Nos. 7,699,508; 7,972,122; 8,007,254; 8,419,609; 8,852,072; and U.S. Pat. Pub. No. 2015/0051438, all of which are incorporated by reference herein as if fully set forth herein.

Figure 5A:
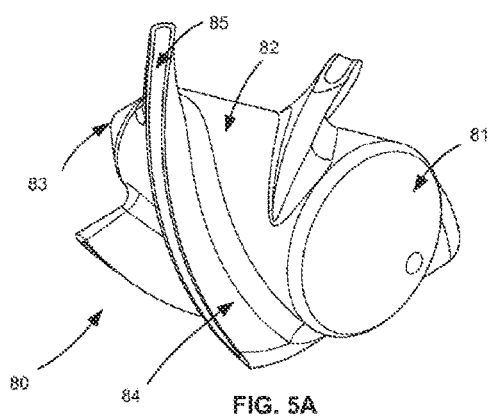
FIGS. 5A, 5B and 5C are views of a diffuser in accordance with one embodiment of the invention.
Figure 5B:
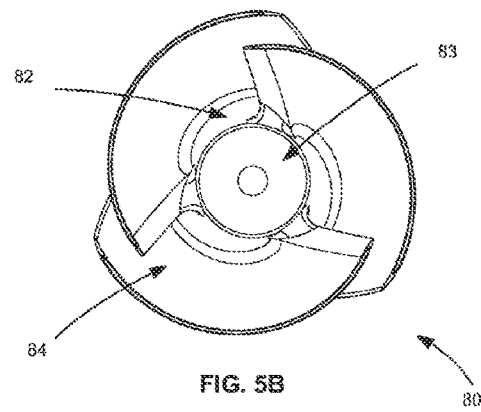
Figure 5C:
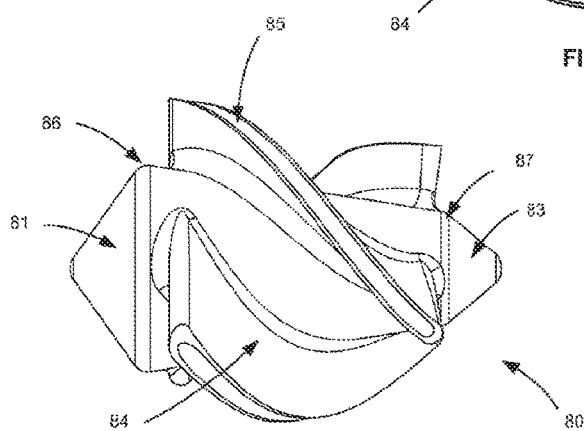

A diffuser 80 is disposed within pump housing 40 as shown in FIGS. 2 and 5A-C. Diffuser 80 is disposed in the housing downstream of impeller 90 between the impeller 90 and outlet 46. In the embodiment illustrated in FIG. 2, diffuser 80 is disposed in the outlet portion 41 of pump housing 40. Diffuser is in alignment with pump housing 40 and axis 11. The diffuser has a body 82 extending along an axis from a first end 86 to a second end 87. In the embodiment shown in FIGS. 5A-5C, body 82 of diffuser 80 is tapered such that body 82 forms a truncated conical shape with a larger cross-section at the first end 86 of the body 82 facing inlet 44 and a smaller cross-section at second end 87 facing outlet 46. Again referring to FIGS. 5A-5C, diffuser also includes conically shaped tips 81, 83 extending from the first and second ends 86, 87 of diffuser body 82, respectively. The extreme tip of each conically shaped tip 81, 83 may be rounded. As illustrated in FIG. 5C, the volume of tip 83 may be smaller than tip 81, though other shapes and volumes are envisioned. A length of diffuser 80 may be between about 0.50 inches and less than 0.85 inches, but preferably about 0.55 inches. The diffuser 80 is formed from materials known to those of ordinary skill in the art.

As shown in FIGS. 5A-5C, body 82 includes at least one vane 84, and preferably a plurality of vanes 84, projecting outwardly from the body 82 and extending along an axial length of the body. The vanes curve around the axis in a substantially helical pattern having a pitch angle which varies along the axial length and is in the opposite direction to the pitch of the blades 92 of the impeller 90. The vanes 84 include a height extending to a peak. The peak tapers from the first end 86 and becomes shorter relative to a longitudinal axis of the diffuser toward the second end 87. A thickness 85 of at least one of the vanes 84 may be any dimension desired, such as for example, about 0.03 inches.

As described above, a pump housing with a tapered outlet portion is shorter than a pump housing without a tapered outlet. For example, the pump housing including a tapered outlet portion 41 can be about 0.30 inches shorter than prior art implantable pumps. In another example, when the diffuser 80 is 0.55 inches in length, the pump housing is approximately 0.36 inches shorter than a pump housing disposed with a diffuser 0.85 inches in length.

Figure 6A:
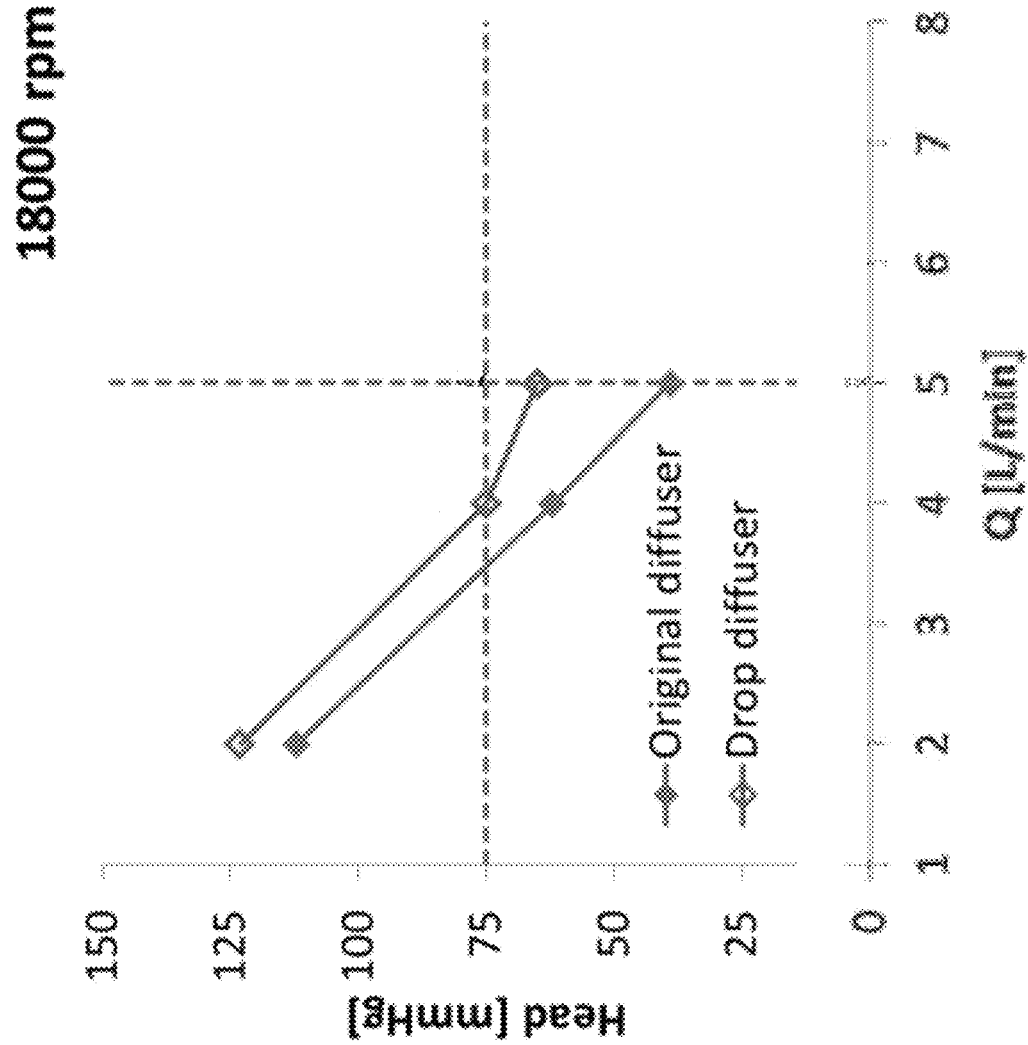
FIGS. 6A and 6B are graphs illustrating results of a "CFD" model comparing pressure head between a prior art diffuser and the diffuser of the present invention (identified as "drop diffuser" in FIGS. 6A and 6B) for a blood pump having an "original impeller" and an "orange impeller," respectively. (CFD, original impeller and orange impeller are discussed further below.)
Figure 6B:
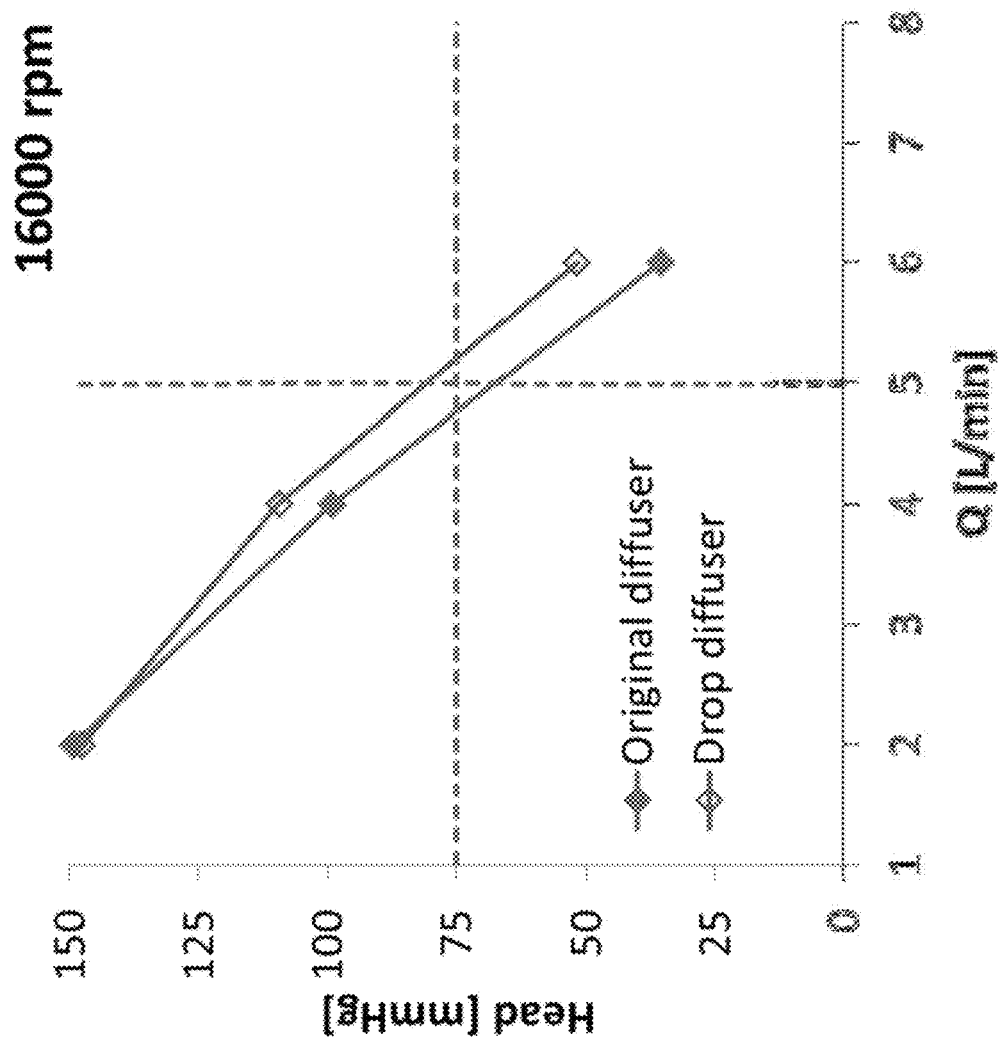

Numerous advantages may be realized with the use of a blood pump that includes an original or orange impeller as disclosed in U.S. Pat. Pub. No. 2015/0051438, incorporated by reference herein as if fully set forth herein, and a diffuser 80 having a tapered diffuser body 82, helical vanes 84 extending outward therefrom and a pump housing with a tapered outlet portion 41. One advantage is improved hydraulic performance, i.e., a net increase in pressure head, through pump housing 40. Using a computational fluid dynamics (CFD) model, performance of diffuser 80 was evaluated relative to a diffuser having a linear body and at least one perpendicular blade (not shown) disposed in a pump housing shaped parallel with axis 11 (i.e., cylindrical housing, not shown). The latter type of diffuser will hereinafter be referred to as an "original" diffuser. The CFD model geometry was developed from the 3D SolidWorks model of the pump by simplifying the geometry to obtain the fluid domain and the corresponding walls. Steady state solutions were obtained for the fluid properties of 2.6 cP viscosity and 1045 kg/m3 density. For a blood pump having the original impeller operating at a rotational speed of 18000 rpm and a flow rate of 5 L/min, pressure head increased from 39 mmHg to 65 mmHg when diffuser 80 replaced original diffuser. Similarly, for an orange impeller at a rotational speed of 16000 rpm and a flow rate of 6 L/min, pressure head increased from 36 mmHg to 52 mmHg when diffuser 80 replaced original diffuser. Pressure head was improved with the use of diffuser 80 over a range of flow rates in combination with either the original impeller or orange impeller, as shown in FIGS. 6A and 6B. The term drop diffuser, as used in FIGS. 6 to 9, is intended to refer generally to diffuser 80.

Figure 7A:
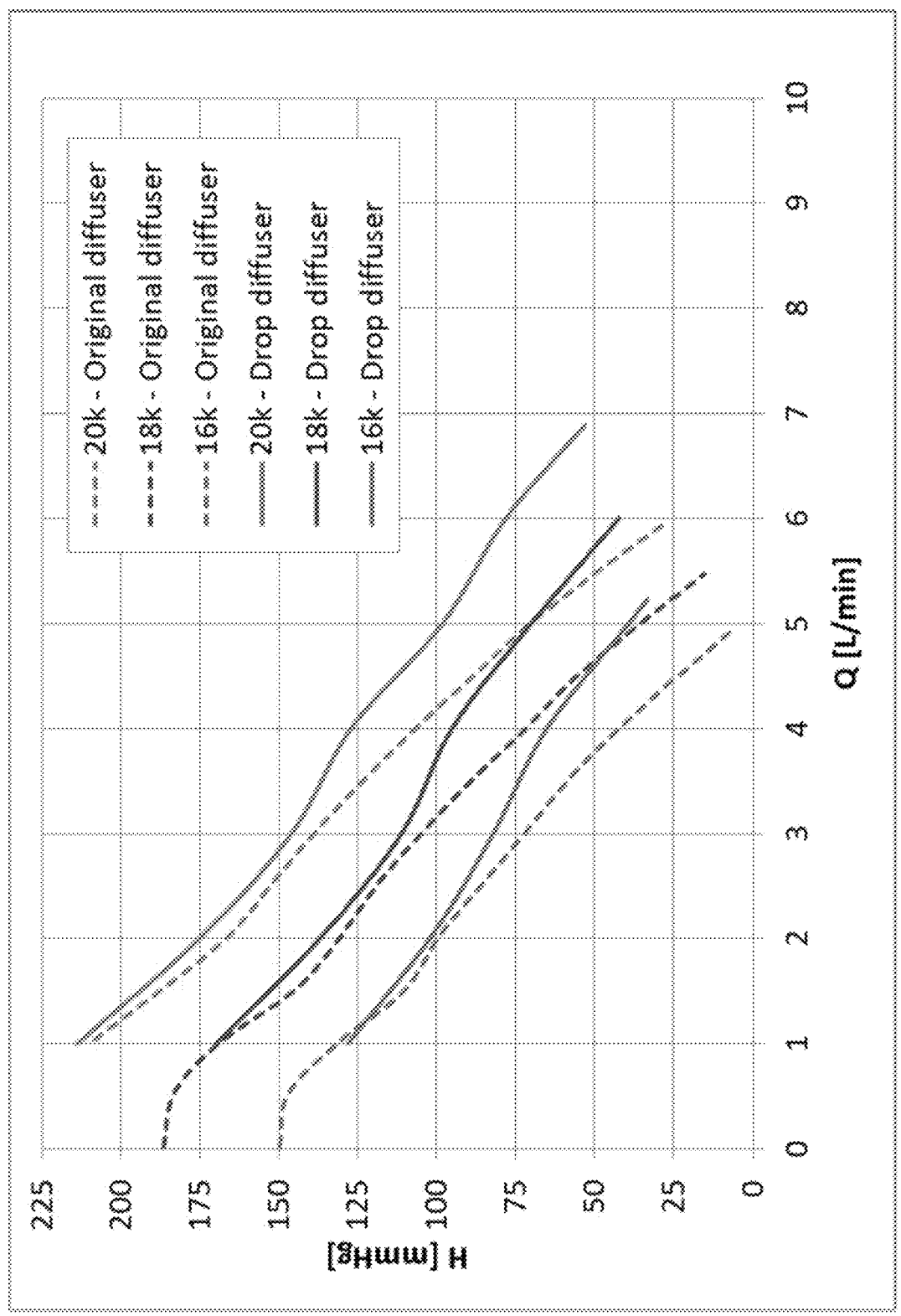
FIGS. 7A and 7B are graphs illustrating results of an "SLA" analysis comparing pressure head between a blood pump having a prior art diffuser and a blood pump having the diffuser of the present invention (drop diffuser) at different rotational speeds for a blood pump using an original impeller and an orange impeller, respectively. (SLA is discussed further below.)
Figure 7B:
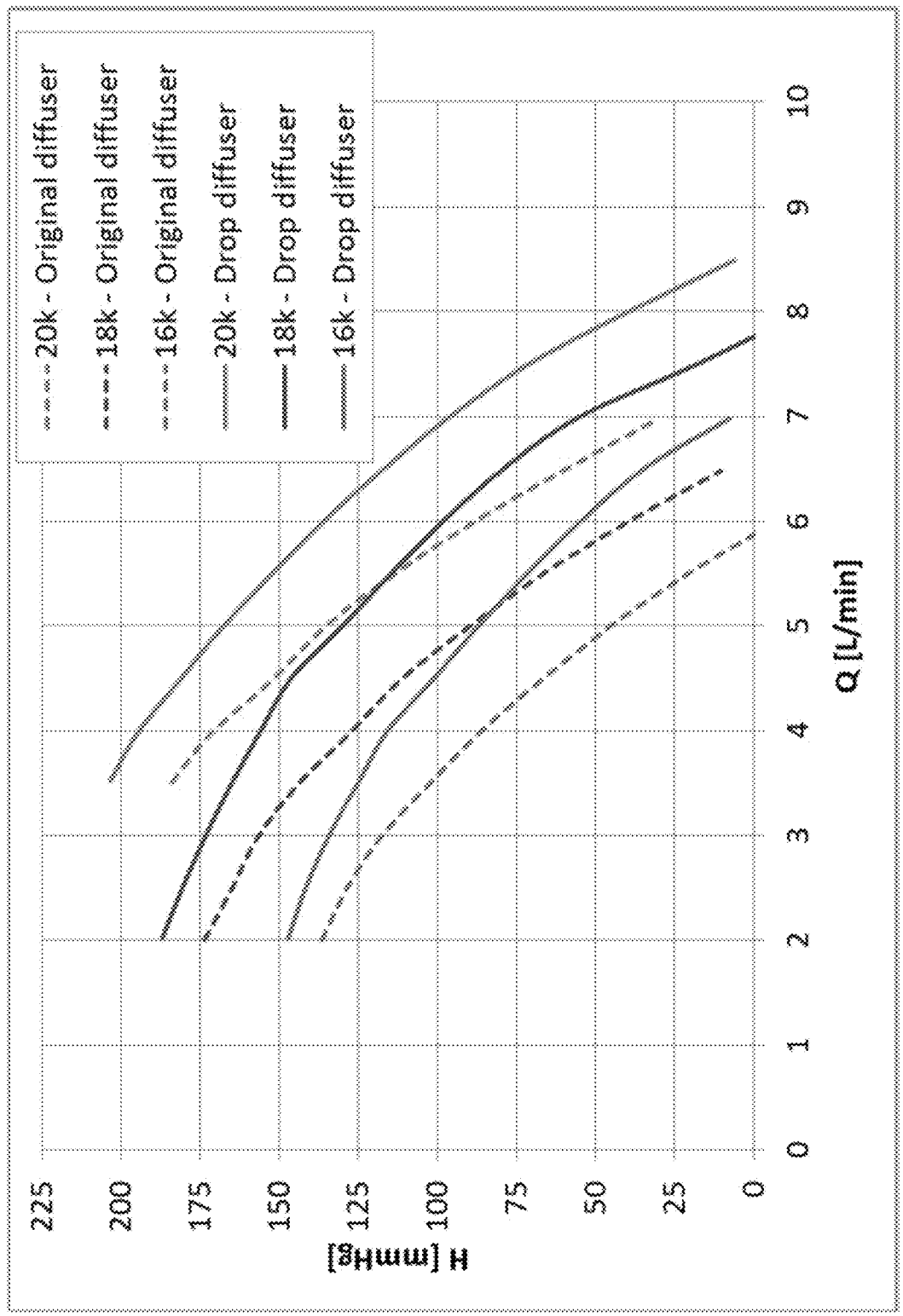

As another example, the improved performance of diffuser 80 in the blood pump was also established through a high-resolution stereograph (SLA) analysis. This analysis was performed using 40/60% water/glycerol solution which provided 2.7-2.8 cP fluid viscosity at 37 C. For an original impeller operating at a rotational speed of 16000 rpm and a flow rate of L/min, pressure head increased from 6 mmHg to 40 mmHg when diffuser 80 replaced original diffuser. Pressure head was similarly improved at rotational speeds of 18000 and 20000 rpm, as shown in FIG. 7A. For an orange impeller operating at a rotational speed of 16000 rpm and a flow rate of 6 L/min, pressure head increased from −6 mmHg to 55 mmHg when diffuser 80 replaced original diffuser. Again, pressure head was similarly improved at rotational speeds of 18000 and 20000 rpm, as shown in FIG. 7B. Table 1 below shows that pressure head for blood pumps incorporating diffuser 80 can be maintained at similar levels to that of blood pumps with original diffuser, even with lower rotational speeds.

TABLE 1

| Impeller | Diffuser | Speed [rpm] | Flow [L/min] | Head [mmHg] | $V_T>$ 150 Pa [mm3] | A wss < 1 Pa [mm2] |
|---|---|---|---|---|---|---|
| Original | Original | 20000 | 5 | 75 | 0.226 | 0.00334 |
| Original | As shown in FIG. 5 | 19000 | 5 | 73 | 0.190 | 0.00001 |
| Orange | Original | 16500 | 5 | 77 | 0.166 | 0.00676 |
| Orange | As shown in FIG. 5 | 15500 | 5 | 73 | 0.156 | 0.00000 |

Figure 8A:
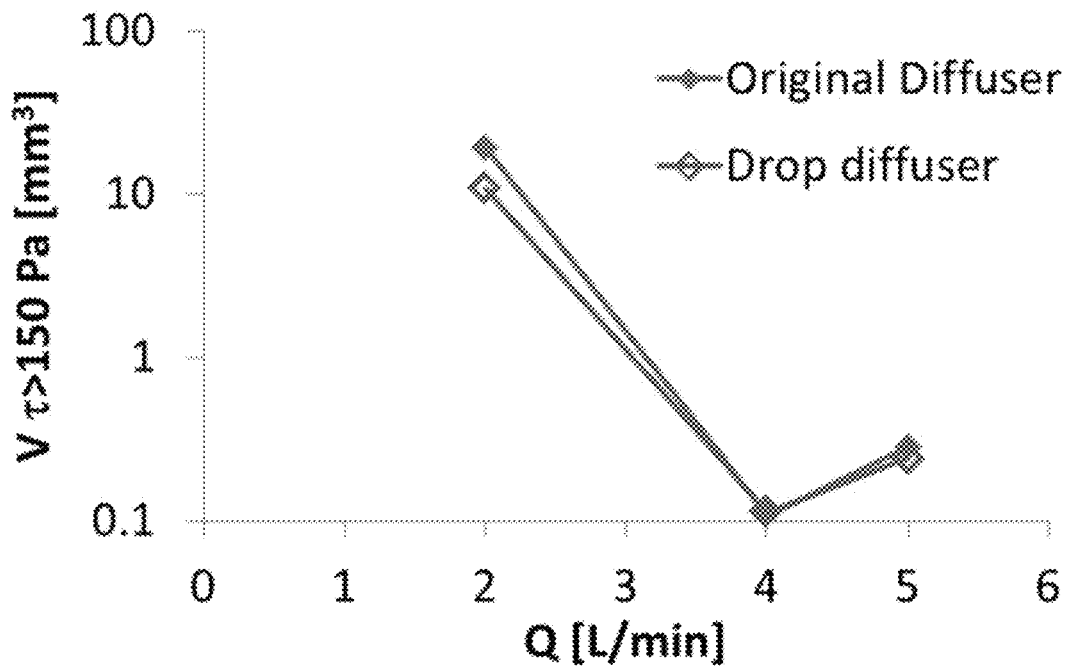
FIGS. 8A, 8B, 8C and 8D are graphs illustrating results of CFD models comparing critical volume and critical area at particular shear stress ranges between a blood pump having a prior art diffuser and a blood pump having the diffuser of the present invention. Results for the present invention are represented by drop diffuser and modified design in the graphs.
Figure 8B:
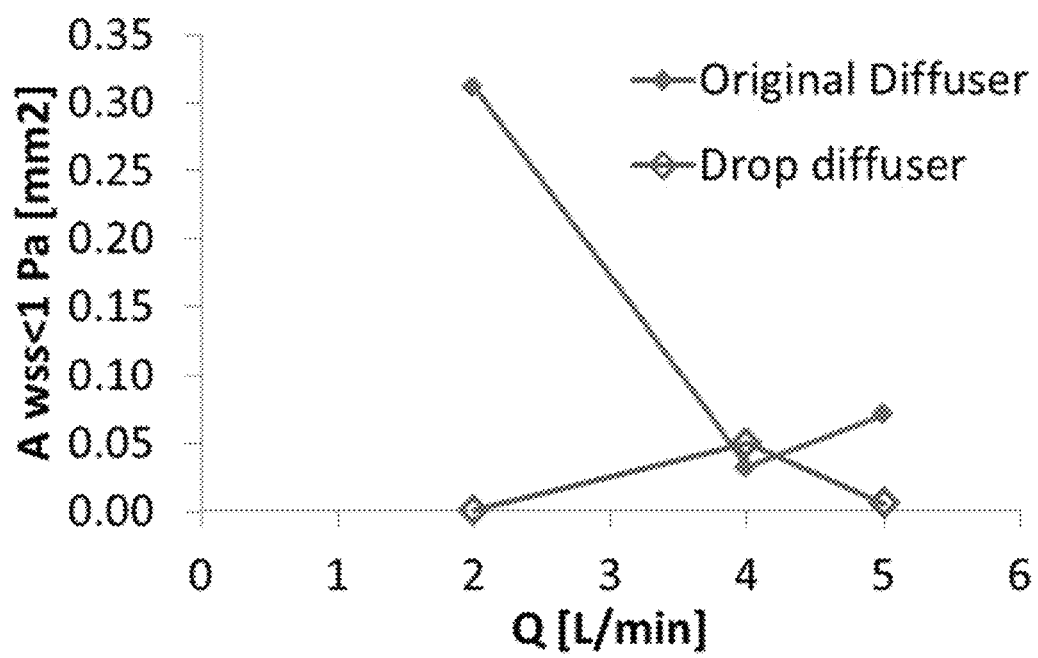
Figure 8C:
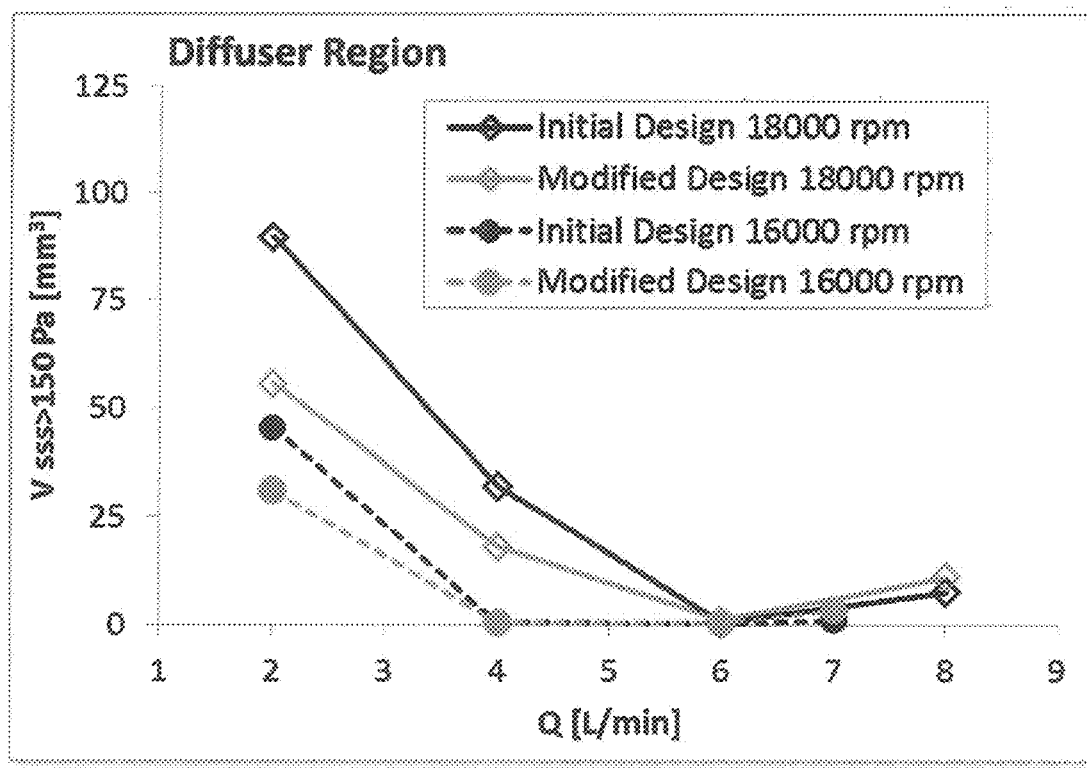
Figure 8D:
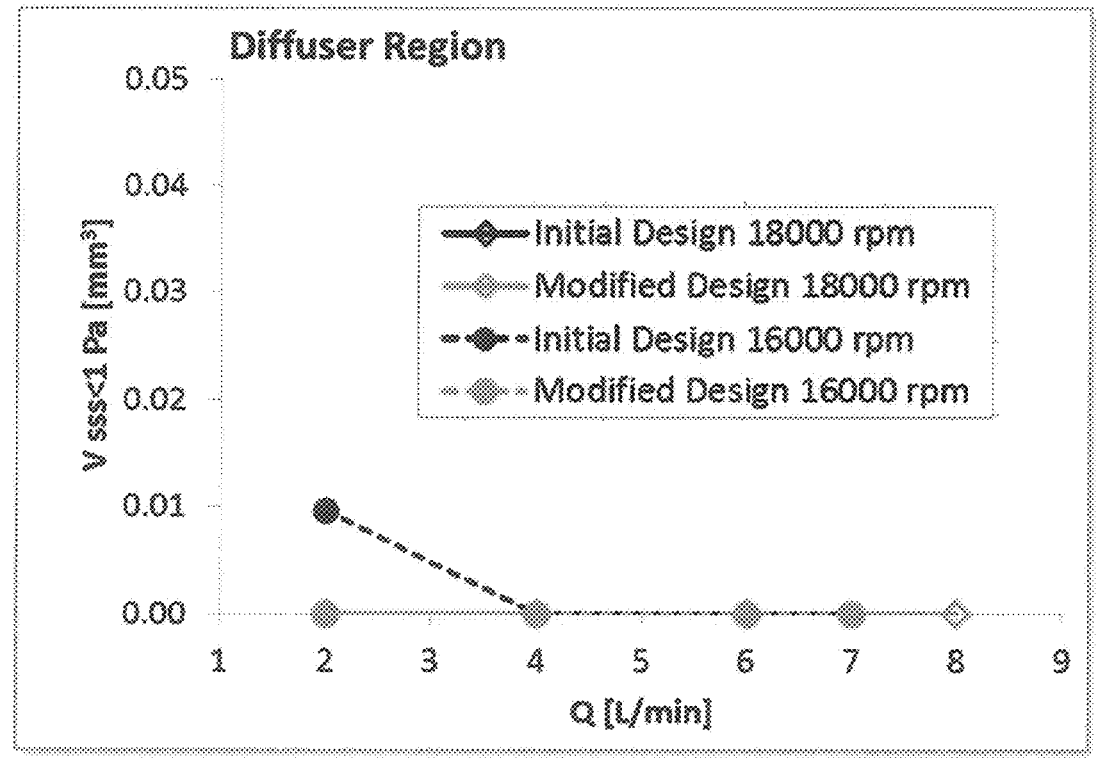

Another advantage of diffuser 80 is reduced exposure to shear stresses above 150 Pa and reduced exposure to wall shear stresses less than 1 Pa for a given flow rate and a given pressure head relative to an original diffuser. This is shown in FIGS. 8A and 8B, particularly toward flow rates of 2 L/min and toward 5 L/min, where a CFD model indicates that critical volume at shear stresses above 150 Pa and critical area at shear stresses below 1 Pa are minimized. The critical volume and area represent the amount of blood in and around the diffuser, including blood between the diffuser and the pump housing which is exposed to shear stresses greater than 150 Pa or wall shear stresses less than 1 Pa. In another CFD model, shown in FIGS. 8C and 8D, diffuser 80 was found to have an improved response to both high and low shear stresses. Lower critical volumes and areas are also apparent from the results as displayed in Table 1 above.

Figure 9:
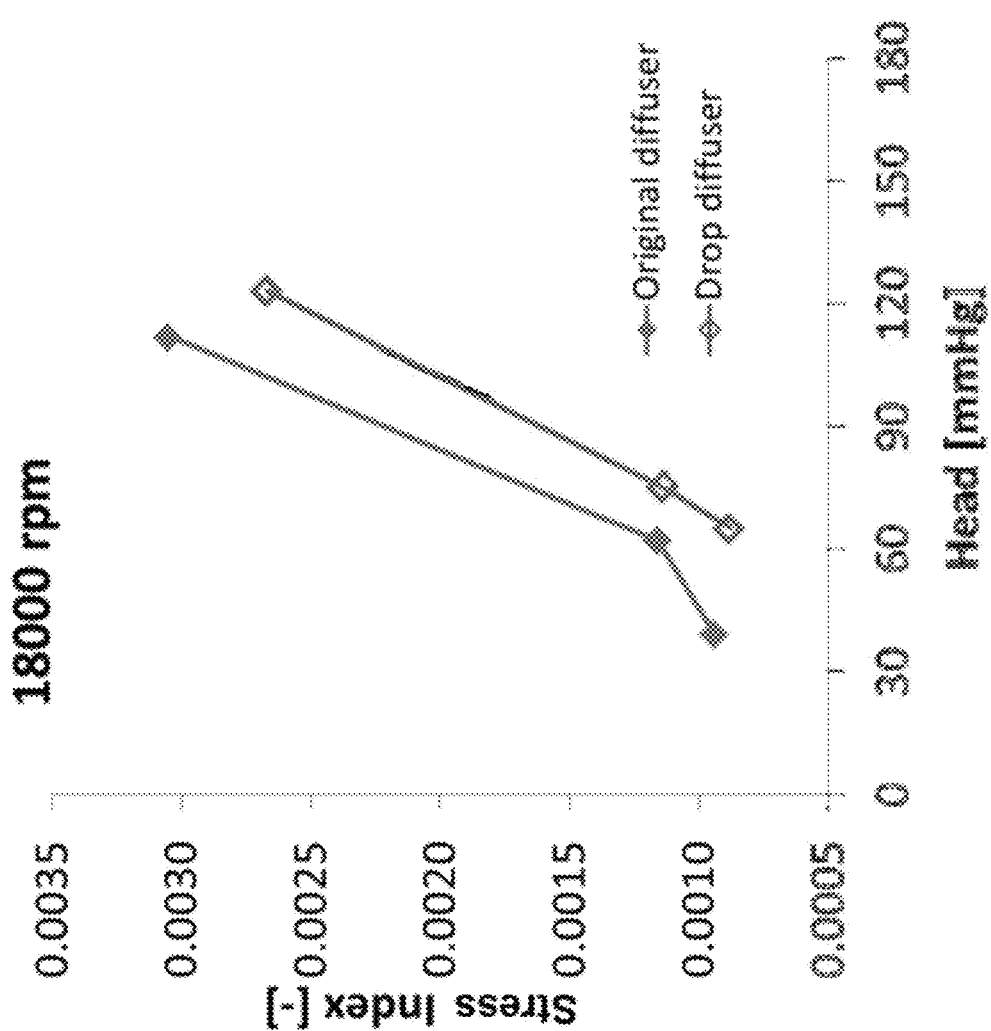
FIG. 9 is a graph illustrating results of a CFD model comparing the stress potential between a prior art diffuser and the diffuser of the present invention (drop diffuser).

Yet another advantage of the blood pumps of the present invention results from the pump having a tapered outlet portion of the pump housing. For example, a blood pump with a housing having a tapered outlet portion 41 may cause less tissue damage during implantation and while implanted and in operation than prior art blood pumps. The diameter of the pump housing 40 is sized so there may be little interaction, or even no interaction, between pump housing 40 and surrounding tissue, including valve leaflets, during operation of the pump 10. Put another way, only outflow cannula 30 extends outside of the left ventricle and into the aorta. FIG. 9 illustrates the reduced stress potential represented by the stress index when diffuser 80 replaces original diffuser as part of implantable blood pump 10. Improved performance occurs at a range of hydraulic function.

Finally, because pump housing 40 allows for a diffuser of shorter length than with prior art blood pumps, outflow cannula 30 may be longer than would otherwise be possible. As a result, greater flexibility is available in the arrangement of pump components and positioning of the blood pump 10. The physical structure of the present invention also improves the ease of use of the pump 10.

Numerous variations and combinations of the features discussed above can be used, some of which are discussed below as examples.

In other embodiments, the outlet portion 41, the central portion 42 and the inlet portion 43 can be of different geometric shapes and different combinations of shapes. For example, the slope of taper of the outer and inlet portions may be steeper or shallower as desired, and may be the same as one another or different from one another. Further, the slope of taper of either of the housing portions may vary along its length (e.g., the slope of the taper of outlet portion 41 varies along its length).

In another embodiment, the outflow cannula 30 can be curved or otherwise nonlinear. The cross-sectional shape of the outflow cannula can be any shape known by those of ordinary skill in the art. For example, see U.S. Pat. No. 8,852,072.

In yet another embodiment, impeller can be disposed at least partially in inlet portion 43 and/or outlet portion 41.

In another embodiment, diffuser can be disposed at least partially in central portion 42.

In another embodiment, the vanes 84 of the diffuser body 82 can be tapered along the axial length of the body such that a peak at the top of the height of the vanes becomes closer to a surface of the body when moving from first end 86 toward second end 87. Alternatively, as illustrated in FIGS. 5A-5C, the peak at the top of the height of the vanes remain the same distance from the surface of the body. Other variations of the relative size and shape of the vanes relative to the surface of the body, or alternatively to a central axis of the diffuser, may be used as desired. In a further embodiment, the thickness of the vanes 84 can be less than 0.03 inches.

In yet another embodiment, Ring 60 can be configured to allow for rotational and/or angular movement, or complete universal movement, of the blood pump 10 to accommodate the native heart movement.

In any of the above embodiments, an inner surface of the housing can taper in parallel to a surface of the body of the diffuser with a cross-sectional area representing the flow path remaining constant at different points along the length of the housing. The flow path surrounding the diffuser has a cross-sectional area measured by taking a cross-sectional area bounded by the inner surface of the housing and subtracting the cross-sectional area of the diffuser inside. The inner surface of the housing can also taper relative to the surface of the body moving toward the outlet end such that the cross-sectional area representing the flow path increases closer to the outlet end. Finally, the inner surface of the housing can converge with the surface of the body moving toward the outlet end such that the area representing the flow path decreases closer to the outlet end. As above, any or all of the tapers can also have a varying slope along their individual length, rather than a constant slope, such that the cross-sectional area representing a particular flow path will change according to the varying taper.

In any of the above embodiments, the first, second, and third portions can be monolithic with one another such that they are formed as a unitary construction during manufacture. Alternatively, the first, second and third portions of the linear housing can also be independent of each other. Also in any of the above embodiments, portions of the first and third portions can be monolithic. For example, the central portion 42 can be monolithic with the outlet portion 41. In one variation, the central and outlet portions can be monolithic while the inlet portion is formed separately such that the impeller and diffuser can be positioned within the housing and can be sealed therein by securing the inlet portion thereto.

In another aspect, a method is provided for manufacturing pump 10. In this method, a cannulated tip 20, a housing 40, an impeller 90 and a diffuser 80 are provided. The housing includes an intake end and an outflow end. The impeller 90 and the diffuser 80 are disposed in the housing 40 and the cannulated tip 20 is attached to the outflow end of the housing 40.

In yet another aspect, a method is provided wherein the implantable blood pump 10 is used to pump blood. In one embodiment of this method, ring 60, extension body 50, pump housing 40 and outflow cannula 30 can be provided as a pre-assembled monolithic unit to facilitate implantation. By way of example, the surgeon gains access to the heart, using a left subcostal or left thoracotomy incision exposing the left ventricular apex. A pledgeted purse string suture is then applied to the epicardium circumferentially over the pump insertion site. A list incision or an incision in the form of a cross or X, commonly referred to as a "crux" incision, is made through the apex of the heart into the interior of the left ventricle using a cutting instrument such as a scalpel. Pump housing 40, extension body 50 and outflow cannula 30 are then inserted through the crux incision or slit incision and positioned within the left ventricle so that cannula 30 extends through the aortic valve into the aorta. Ring 60 is positioned on the outside of the heart (not shown). See, for example, U.S. Pat. No. 8,852,072.

When the blood pump is in the implanted condition, ring 60 is mounted adjacent the apex of the patient's heart. Ring 60 and pump housing 40 are connected to extension body 50 remote from one another so that extension body 50 maintains pump housing 40 in position relative to ring 60. Extension body 50 is sufficiently rigid to maintain the pump housing 40 and outflow cannula 30 in position relative to the heart. The implant and positioning of ring 60 and extension body 50 provide secure positioning of the pump housing 40 and outflow cannula 30 relative to the heart.

In the implanted condition, the outflow cannula 30 projects through the aortic valve into the ascending aorta, but terminates proximal to the arch of the aorta. The shape of pump housing 40 and in particular outflow portion 41 ensures that only the outflow cannula 30 and tip 20 interact with the aortic valve when pump 10 is implanted. The location of pump 10 relative to anatomy can be any location known to those of skill in the art. For example, see U.S. Pat. No. 8,852,072.

Operation is facilitated with the pump implanted in the body of a patient, and with the pump housing 40 connected into the circulatory system as, for example, in the conventional manner for a blood pump, and impeller 90 is actuated using means known in the art and/or those described above. For example, through the use of a power source. The impeller 90 is actuated in a manner so that it spins in the forward circumferential direction. The spinning impeller 90 retrieves and pumps blood from inlet 43 in the downstream direction toward diffuser 80. The spinning impeller also imparts angular momentum to the blood around the central axis 11 of the impeller 90. The operation of impeller 90 can be by any means known to those of skill in the art. For example, see U.S. Pat. Pub. No. 2015/0051438. As the blood encounters the diffuser 80, this angular momentum is converted to axial momentum and pressure head. The one or more vanes 84 of diffuser 80 serve to reclaim the energy used to create the angular motion and convert that energy to useful pumping work. The blood passes through outlet 46 and then through outflow cannula 30 once it is downstream of the diffuser 80, and exits blood pump 10 via cannula tip 20 for further distribution into the arterial system via the aorta. The blood from the left ventricle can be pumped into the aorta through an aortic valve or a bypass conduit.

Advantages of the above method include that pressure head using blood pump 10 is improved relative to prior art blood pumps. Also, critical volume and critical area at shear stresses greater than 150 Pa and at wall shear stresses less than 1 Pa are minimized through the above method using pump 10. Yet another advantage is that the shape of the pump housing 40 in combination with the shape of the diffuser 80 in the above method minimizes damage to tissue surfaces and interaction of pump 10 with the aorta.

In further embodiments, the method described above can be employed using pump housing 40 having portions 41, 42 and 43 of varying shapes and combinations of shapes. In these and still further embodiments, diffuser 80 and the vanes 84 can vary in shape and size as described above.

In still further embodiments, the pump housing 40 can be monolithic and the ring 60, extension body 50 and outflow cannula 30 can be assembled at time of surgery. In a further embodiment, the pump housing 40 can be monolithic with one or more of the ring 60, extension body 50, and/or outflow cannula 30. Finally, in other embodiments, combinations of the portions of the pump housing 40 can be assembled at the time of surgery.

Any of the above embodiments can include an implantable blood pump 10 implanted in areas of the vasculature other than the left ventricle or in areas adjacent to the vasculature.

The invention described herein provides at least three advantages. First, an implantable blood pump including a tapered housing and a tapered diffuser with a length shorter than traditional diffusers still provides increased blood pressure through the pump and into a patient's bloodstream than what could be done using prior art pumps. This is evidenced by the performance of the pump relative to prior art pumps as shown in FIGS. 6A, 6B, 7A and 7B. Second, the pump as described above also reduces the risk of blood clotting in the pump because the structural features prevent platelet aggregation in the blood. This makes the pump much safer for patients, and is supported by test data as illustrated in FIGS. 8A to 8D. Third, the pump including the tapered housing and the diffuser minimizes stress potential caused while the pump is implanted in a patient, as is shown in FIG. 9.

All publications, provisional patent applications, patent application publications and issued patents cited above are incorporated herein by reference as if fully set forth herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. An implantable blood pump, comprising:
a housing having an intake end, an outflow end, and a tapered outlet portion between the intake end and the outflow end;
a cannulated tip extending from the outflow end of the housing;
an impeller disposed in the housing; and a diffuser disposed in the tapered outlet portion of the housing, the diffuser including:
a tapered body having a first end, a second end opposite the first end, and a tapered portion extending from the first end to the second end, the tapered body including at least one vane disposed thereon;
a first conically shaped tip extending from the first end of the tapered body toward the intake end; and
a second conically shaped tip extending from the second end of the tapered body toward the outflow end.

2. The implantable blood pump of claim 1, wherein the housing includes a first portion adjacent the intake end, a second portion adjacent the outflow end, and a third portion between the first and second portions, wherein a cross-sectional area of the first portion is greater than a cross-sectional area of the second portion, and a cross-sectional area of the third portion decreases in a direction from the first portion to the second portion.

3. The implantable blood pump of claim 2, wherein the housing is linear.

4. The implantable blood pump of claim 3, wherein the diffuser is disposed within the third portion of the housing.

5. The implantable blood pump of claim 4, wherein the cross-sectional area of the first, second and third portions is circular.

6. The implantable blood pump of claim 5, wherein an inner surface of the third portion of the housing tapers toward the outflow end in parallel with a surface of the tapered body of the diffuser such that the cross-sectional area of a flow path between the inner surface of the third portion and the diffuser is approximately the same at any point along a length of the body of the diffuser.

7. The implantable blood pump of claim 1, wherein the tapered body of the diffuser has a truncated cone shape.

8. The implantable blood pump of claim 7, wherein a cross-sectional area of the tapered body of the diffuser is largest at an intake end of the tapered body.

9. The implantable blood pump of claim 8, wherein a length of the diffuser is between about 0.50 inches and less than 0.85 inches.

10. The implantable blood pump of claim 1, wherein the first conically shaped tip includes a volume larger than a volume of the second conically shaped tip.

11. The implantable blood pump of claim 10, wherein the tapered body of the diffuser includes the at least one vane positioned along a surface defined along a length of the tapered body.

12. The implantable blood pump of claim 11, wherein the at least one vane further comprises a peak having a height extending outward in a perpendicular direction from the surface of the tapered body, the height tapering along the length of the tapered body in a direction toward the outflow end.

13. The implantable blood pump of claim 12, wherein the height of the at least one vane along the length of the tapered body tapers relative to the surface of the tapered body of the diffuser.

14. The implantable blood pump of claim 12, wherein the height of the at least one vane along the length of the tapered body tapers relative to a longitudinal axis of the diffuser.

15. The implantable blood pump of claim 12, wherein at least one of the at least one vane has a thickness of about 0.03 inches.

16. The implantable blood pump of claim 12, wherein the length of the diffuser is about 0.55 inches.

17. The implantable blood pump of claim 1, further comprising a length of the first conically shaped tip being about the same as a length of the second conically shaped tip, wherein the length of each of the first and second conically shaped tips is measured along a longitudinal axis of the tapered body.

18. An implantable blood pump, comprising:
a housing having an intake end, an outflow end, and a tapered outlet portion between the intake end and the outflow end;
an impeller disposed in the housing; and
a diffuser disposed within the tapered outlet portion of the housing, the diffuser including a tapered body, a first conically shaped tapered tip extending from the tapered body in a direction toward the intake end, and a second conically shaped tapered tip extending from the tapered body in a direction toward the outflow end, the tapered body having an angle different than an angle of the first conically shaped tapered tip.

19. The implantable blood pump according to claim 18, wherein the tapered body includes at least one vane disposed thereon.

* * * * *